United States Patent [19]

Wills

[11] Patent Number: 5,413,117
[45] Date of Patent: May 9, 1995

[54] PROPHYLACTIC DEVICE

[76] Inventor: Marquita Wills, 724 Leavenworth St., Apt. K, San Francisco, Calif. 94109

[21] Appl. No.: 286,642
[22] Filed: Aug. 5, 1994
[51] Int. Cl.6 .................. A61F 6/06; A61F 6/02
[52] U.S. Cl. .................. 128/830; 128/842
[58] Field of Search ........ 128/842, 844, 918, 830–841; 604/330, 347–353

[56] References Cited

U.S. PATENT DOCUMENTS

| | | | |
|---|---|---|---|
| 1,928,175 | 9/1933 | Hailey | 604/347 |
| 2,277,043 | 3/1942 | Cohn | 604/348 |
| 2,484,356 | 10/1949 | Ribeiro | 604/347 |
| 3,374,790 | 3/1968 | Mayhorne | 604/347 |
| 3,577,989 | 5/1971 | Anderson | 604/348 |
| 4,031,897 | 6/1977 | Graetz | 604/347 |
| 4,886,508 | 12/1989 | Washington | 604/347 |
| 5,111,831 | 5/1992 | Foggia | 128/842 |
| 5,113,873 | 5/1992 | Boarman | 128/830 |
| 5,121,755 | 6/1992 | Hegedusch | 128/844 |
| 5,156,165 | 10/1992 | Wu | 128/844 |
| 5,163,449 | 11/1992 | van der Walk | 128/844 |
| 5,168,881 | 12/1992 | Reddy | 128/844 |
| 5,181,527 | 1/1993 | Dorsey | 128/844 |

*Primary Examiner*—Michael A. Brown
*Attorney, Agent, or Firm*—Ray K. Shahani

[57] ABSTRACT

A prophylactic device for humans which will allow penetration of body cavities or other orifices especially during sexual activity intended to reduce communication of body or other fluids between a user and a partner. A fluid impervious shield member lies or drapes over the pubic region or other region surrounding the cavity or orifice to be penetrated, the shield member having on one side a fluid absorbing element for capturing body or other fluids produced by or applied to the body cavity or orifice during such activity. A central opening in the device has a slotted elastic member placed over and sealing the opening, the slotted elastic member having a small slot which will allow penetration of the body cavity or other orifice, the elastic material of the slotted elastic member being sufficiently rigid and flexible to provide squeegee or wiping action on the item being used for penetration, thereby preventing fluids from being withdrawn from the body cavity or other orifice and communicated to a partner.

16 Claims, 3 Drawing Sheets

PROPHYLACTIC DEVICE

BACKGROUND OF THE INVENTION

1. Field of the Invention

The present invention relates to a prophylactic device for humans, and more particularly, to a prophylactic device which will allow penetration of body cavities or orifices by a probing item, especially during sexual activity, but will reduce communication of body or other fluids.

2. Prior Art

U.S. Pat. No. 5,111,831, class 128/842, issued May 12, 1992 to Foggia teaches a scrotum supporting condom with retention means comprising a rollable condom having a retention periphery at the open end of an elongated tubular sheath, the open end having a discontinuity between the end of the sheath and the peripheral bead, such that when the sheath is unrolled onto an erect penis and the scrotum positioned through the discontinuity between the sheath and the retaining bead, support is provided to the scrotum thereby achieving increased physical contact during use.

U.S. Pat. No. 5,113,873, class 128/830, issued May 19, 1992 to Boatman teaches a contraception and prophylaxis enhancement system for use by women, having a one-piece formation, and comprising an extended tubular member with fluid absorbing material and a genital shield member, and also comprising a mechanism for inserting and retaining the tubular member within the vaginal cavity.

U.S. Pat. No. 5,121,755, class 128/844, issued Jun. 16, 1992 to Hegedusch teaches a reinforced tethered condom construction for male genitalia comprising a conventional condom sheath which is provided with a pair of elongated tether elements secured on the inside of the condom sheath to provide lateral reinforcement along a substantial portion of the condom sheath and wherein the free ends of the tether elements are dimensioned to both encircle and be secured to the users genitalia.

U.S. Pat. No. 5,156,165, class 128/844, issued Oct. 20, 1992 to Wu teaches a birth control and disease preventing device having a large elastic pubic shield integrated about a central toroidal ring which is integrated about the open end of a portion configured as a conventional condom, the upper portion of the large elastic shield being securable about the user's waist while the lower portion of the shield has two movable portions, each securable to the user's legs to improve the protection of the areas around the pubic and the scrotum when the user's legs are in different positions.

U.S. Pat. No. 5,163,449, class 128/844, issued Nov. 17, 1992 to van der Valk teaches a device for a male condom, and a condom to the used with this device which comprises essentially a rigid, two-part ring with a releasable connection which fits loosely at the base of the erect penis such that when a conventional or specially adapted condom is unrolled over the erect penis, the releasable connection forms an attachment means securing the peripheral bead at the open end of the condom to the rigid ring.

U.S. Pat. No. 5,168,881, class 128/844 issued Dec. 8, 1992 to Reddy teaches a prophylactic device comprising a rolled elongated sheath portion circumferentially integral with a broad flange member with attachment means such that the user can unroll the sheath member either over an erect penis or as the vaginal cavity is penetrated.

Finally, the conventional "oral dam" consists merely of a sheet of elastic, plastic, rubber or similar material placed over portions of an individuals genitalia during sexual contact to prevent the communication of body fluids. This type of device has become widely used and depended upon by numerous individuals. It is easy to use and inexpensive to manufacture, distribute and purchase. Several drawbacks exist, however, to the use or reliance upon this type of device. Namely, there is no way to secure the dam to a wearer—one must maintain manual control of the piece of rubber in order to keep it in place. Furthermore, there is no way for this device to absorb body fluids and any fluids produced during sexual activity must be avoided or removed using secondary means. Finally, using an oral dam does not allow significant penetration and any penetration which occurs is likely to cause damage to the oral dam.

A fundamental medical and health concern in today's society is the prevention of the spread of sexually transmitted diseases (STDs). The tremendous explosion of the acquired immune deficiency syndrome (AIDS) epidemic has caused modern man and woman to change their sexual practice to incorporate "safe sex". This term has come to mean sexual activity wherein the sexual partners take personal responsibility for themselves and their partners to ensure that there is no possible way for sexually transmitted diseases to infect themselves or their partners. There is a range of activities which can be said to be more safe and less safe but it is generally well accepted that the most effective way to prevent transmission of disease is by reducing the exchange of body fluids. These concepts are similar to certain most traditional forms of contraception, including the use of the condom. However, scientific data has demonstrated that the AIDS virus is transmitted via the exchange of body fluids.

The condom has been one of the most important devices for preventing the spread of STDs. There are numerous drawbacks to using a condom, however, including the possibility of breakage or slippage. Furthermore, a condom will not prevent communication of body fluids to the pubic, anal or other regions and condoms are generally intended for use by men.

In sum, aside from a few minor variations, as indicated by some of the patents in the prior art, the prevention of STDs and the exchange of bodily fluids has been predominantly dependent on these few devices. An important factor which needs to be mentioned is the moral position taken by important forces in society. For a long time in most of modern society, including Western civilizations as well as those of Asia, Africa and elsewhere, there has been a legal and moral prohibition on sexual activity not directed toward procreation, sexual activity among unmarried couples, sexual activity among youth and senior citizens, sexual activity between partners of the same sex, and other sexual practices. These past prohibitions have stifled an increase in related technology and the availability of alternative sexual devices which are required in a responsible modern society. However, as modern society has developed, in no small way influenced by a number of factors including the so-called "sexual revolution" of the 1960s and 1970s, the increase in tolerance toward people in our society of different sexual orientations juxtaposed against a political and religious fundamentalism and intolerance, and other factors, a controversy between these different elements in society regarding sexual freedom and expression now exists. It does not appear that this controversy will soon be resolved nor does it appear that either side is gaining significant ground. However, common mores and values do exist between all people in all societies, including the need to maintain a medically healthy population, the need to have each and every member of society take responsibility and account for their behavior, and, perhaps the most fundamental of all, the requirement that all members of society treat each other member with respect. It would appear that society has recognized these basic values and that a greater tolerance for individual lifestyles will result. Thus, a need exists in today's society for a greater number of prophylactic devices to give individuals in our society a greater range of options for their own particular lifestyles.

SUMMARY OF THE INVENTION

The present invention relates to a prophylactic device for humans which will allow penetration of body cavities or orifices by any probing item, especially during sexual activity, but will reduce communication of body or other fluids from a user to a partner, comprising: a shield member constructed out of a first fluid impervious material and having an upper side and a lower side, the shield member having a predetermined size and shape suitable for covering pubic and other regions surrounding body cavities and orifices, thereby reducing the communication of body or other fluids therethrough; a fluid absorbing element having an attachment face and a fluid absorbing face, the attachment face attached to the lower side of the shield member; a central opening extending through both the shield member and the fluid absorbing element, the central opening having a predetermined size and shape, the central opening having a peripheral edge extending a short distance from the central opening; and a slotted elastic member being constructed of the same or of a second fluid impervious material, the second fluid impervious material being somewhat rigid, the slotted elastic member being somewhat larger in size than the central opening, the slotted elastic member being attached to the shield member in a region about the peripheral edge of the central opening thus forming a seal between the peripheral edge of the central opening and the slotted elastic member, thereby reducing the communication of body or other fluids between the slotted elastic member and the shield member, the slotted elastic member having a slot with a predetermined length extending therethrough, the slot forming two opposing edges, the slotted elastic member being adequately rigid so as to maintain the opposing edges adjacent to and in contact with each other, thereby reducing the communication of body or other fluids therethrough, whereby when the prophylactic device is placed over the pubic or other regions surrounding cavities or orifices to be penetrated, during the penetration accompanying the sexual activity by the probing item the slotted elastic member produces a squeegee or wiping action to remove the body or other fluids from the probing item thereby reducing the communication of body or other fluids therethrough.

The invention further comprises a retaining means for retaining the prophylactic device in place on the user, the retaining means comprising a plurality of extending sections having a predetermined length. The extending sections may comprise a flexible material and the predetermined length of the extending sections is adequate to encircle portions of a user's body, a user's legs, a user's waist or a user's head. The retaining means can also comprise an adhesive.

The slot is between approximately ½ and 3 inches in length and the first and second fluid impervious materials comprise a polymeric material, a natural material or a rubber material. The fluid absorbing element comprises an absorbing pad or an absorbing material. It is important to note that the central, slotted area of the device, while being somewhat more rigid than a single piece of latex or plastic in order to effect the squeegee action, must not be too rigid. In this manner, a tongue or other organ or apparatus being inserted through the slotted portion will not be constricted or prevented from operating as intended.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE INVENTION

DETAILED DESCRIPTION OF THE PREFERRED EMBODIMENTS

Figure 1:
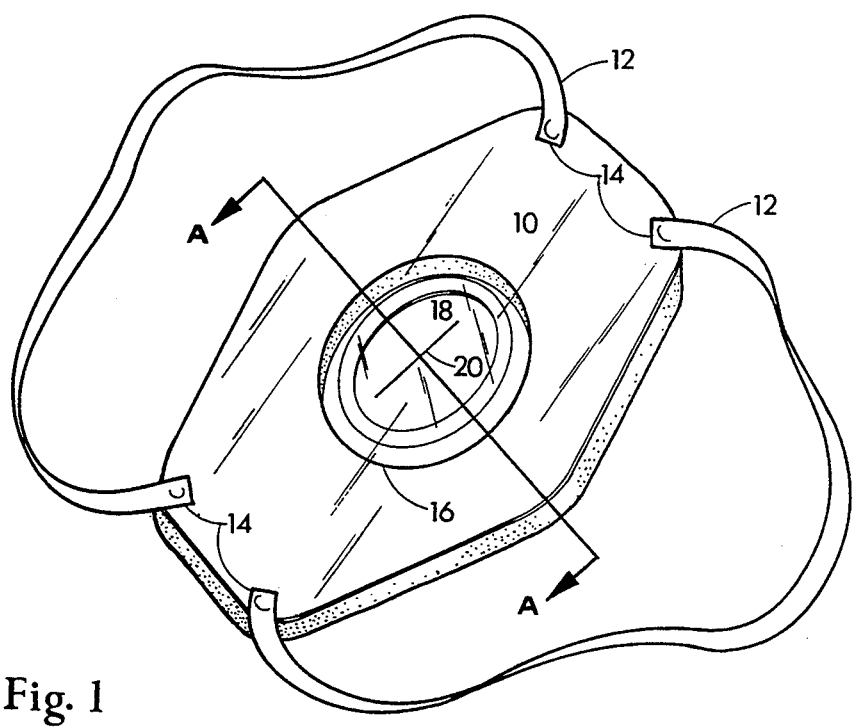
FIG. 1 shows a perspective view of the upper side of an embodiment of the present invention.

FIG. 1 shows a perspective view of the upper side of an embodiment of the present invention. A flexible and fluid impervious shield portion 10 is the primary barrier to exchange of body fluids. Typically this portion would be constructed out of latex or some other type of rubber, plastic or polymeric material. Important health and safety considerations when choosing the material must be made and include compatibility with human contact and body fluids and compatibility with lubricating or contraceptive creams, jellies or other chemicals and substances. Finally, the structural integrity of this shield portion is very important and the construction design must take into consideration the relative tensile strength of the material, the durability of the material during activity, the storage and transportation requirements for the product which may include elevated or depressed temperatures and other environmental conditions.

Retaining straps 12 are attached to the shield portion at points 14. These straps would be worn over the user's legs, as in FIGS. 4 and 5, or waist, head or other body part. The points of attachment can be made by any means known to those skilled in the art and would be specifically adapted for moist and wet conditions, attachments between flexible materials and attachments undergoing a considerable amount of stress as the device is put on a user and as the device is being used, and might include adhesives, stitching, integral molding, rivets, snaps or buttons, or other means. Any other means known to those skilled in the art for retaining the device in position during sexual activity would also be contemplated, and include rigid extending members for clipping onto a user's legs or waist or head, adhesives placed on the outer periphery of the shield member thereby eliminating the need for any straps or clips but perhaps providing less security and retaining power, etc.

A central, generally circular opening 16 in the shield is covered by a slotted elastic member 18 with a central slot 20. The presence of the slot is one of the key features of the invention and one of the most important reasons why this invention, alone, cannot be used as a contraceptive device. It is this slot which allows penetration through the device. The slotted elastic member may be constructed out of the same fluid impervious material as is found on the top side of the invention, as discussed above. Alternatively, a heavier, thicker or semi-rigid piece of elastic material could be used. In this manner, the thickness or rigidity of the element will maintain the slot in a more or less closed position unless penetration occurs.

The slotted elastic member would be attached to the lower side of the invention and can be either attached to the fluid absorbing element or to the central region of the shield portion (as will become apparent by the following). It will be understood that in one embodiment, the slotted elastic member completely covers the central, generally circular opening in the shield member and the fluid absorbing element. However, if the entire shield portion and slotted member were both one and the same piece of material, then no separate central opening would exist in the prophylactic device. In that case, a large, typically latex or other elastic material, shield portion with a slot would have the fluid absorbent material on one side and retaining straps for security.

Figure 2:
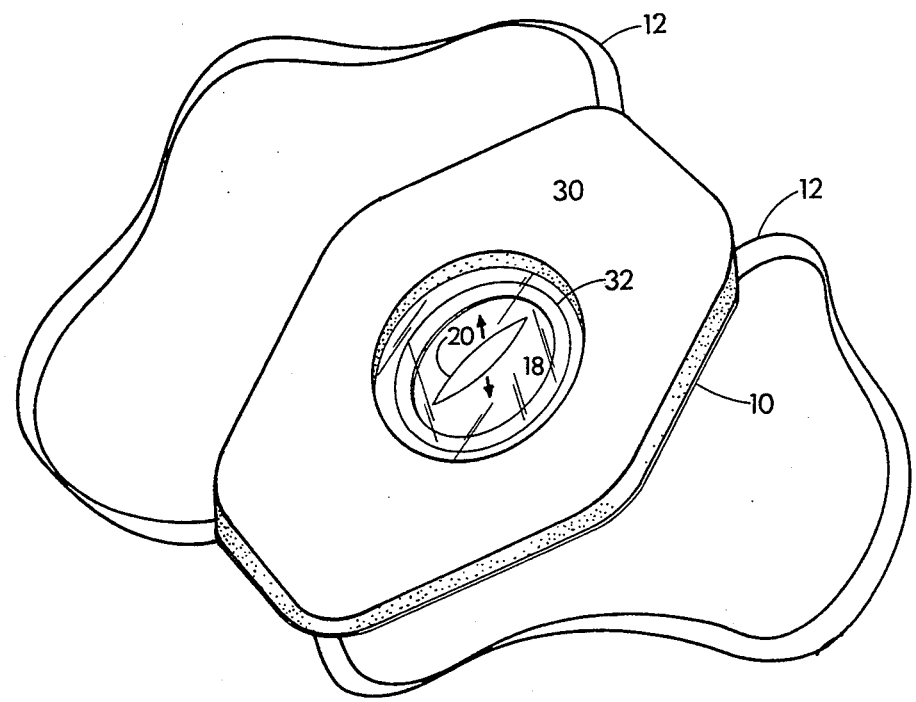
FIG. 2 shows a perspective view of the lower side of an embodiment of the invention.

FIG. 2 shows a perspective view of the lower side of an embodiment of the invention. Fluid absorbing element 30 is attached to the shield portion (not shown) and also has a central, generally circular opening. This attachment can be any means known to those skilled in the art and would be specifically adapted for moist and wet conditions, attachments between flexible materials and attachments undergoing a considerable amount of stress as the device is put on a user and as the device is being used, and might include adhesives, stitching, integral molding, or other means. The material of construction chosen for this fluid absorbing element must be chosen with care and considerations would include some of those made with respect to the fluid impervious shield portion. Additionally, the element must be suitably absorbent so as to prevent leakage or dripping. Well known advances in medical bandages and wound dressings, feminine hygiene inserts and pads, infant diapers, home supplies and other fields have made available a wide variety of suitable materials for providing great absorbance and retention capacity while maintaining a thin, lightweight, flexible, economic and functional design. Thus, the fluid absorbing element might consist of a fluid absorbing pad, a fluid absorbing material or chemical, etc.

Figure 3:
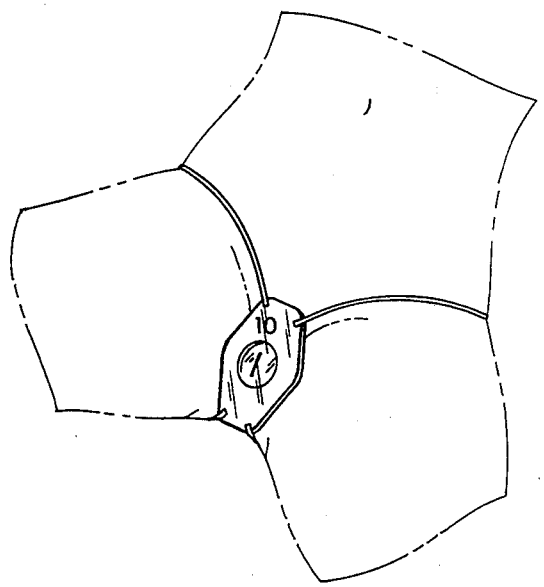
FIG. 3 shows a perspective view of an embodiment of the invention as being used by a female.

FIG. 3 shows a perspective view of an embodiment of the invention as being used by a female. It will be understood that the invention is intended for vaginal protection and penetration, anal protection and penetration, oral protection and penetration, as well as protection and penetration of other cavities or orifices. As shown, the lower surface is oriented toward the user. In this manner, the vagina or other orifice is considered to be the main source of body fluids from which protection is being sought. However, there will also be protection provided from communication of fluids from the top, fluid impervious side which comprises the shield portion 10. It would also be possible to construct the invention such that a second fluid absorbing element is placed on the top side. In the embodiment shown, the fluids produced by or applied to the female genitalia would be absorbed by the fluid absorbent element. In this fashion, protection from contact with body fluids is possible even when no penetration occurs. Manual or other physical contact between a user and the user's partner is frequent during sexual activity and the semi-rigid slotted elastic member would remain closed. Though there is no separate closure to the slot, the semi-rigid nature of the member prevents a most of the fluids being produced from passing through the slot, and therefore, caressing or fondling or other contact will be protected to a certain degree. Any penetration or rougher, more physical activity, if not for the semi-rigid slotted member, would allow fluid to seep through the slot and accumulate on the upper, fluid impervious shield portion of the invention.

Figure 4:
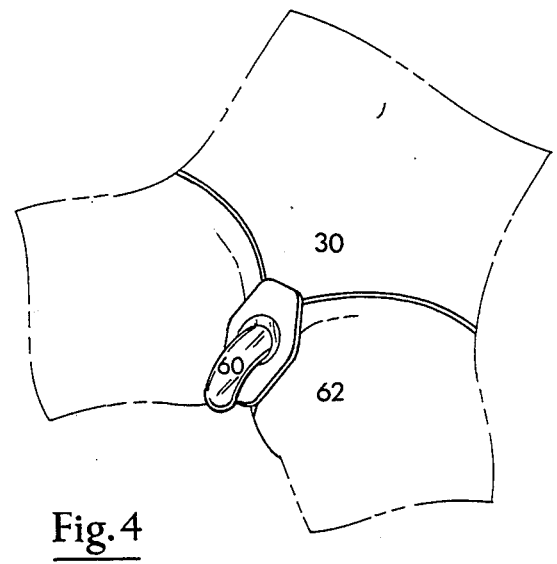
FIG. 4 shows a perspective view of an embodiment of the invention as being used by a male.

FIG. 4 shows a perspective view of an embodiment of the invention as being used by a male. In this method of use of the invention, the male penis 60 would extend through the slotted elastic member. It is intended that the user would also be wearing a condom. A seal 62 would be created between the base of the condom and the slotted elastic member. Fluid absorbing material 30 would be exposed. Thus, as in the embodiment shown, this invention will prevent fluids being produced by the orifice being penetrated or other fluids applied to the male organ, from being communicated to the legs, pubic or anal regions of the male partner.

Figure 5:
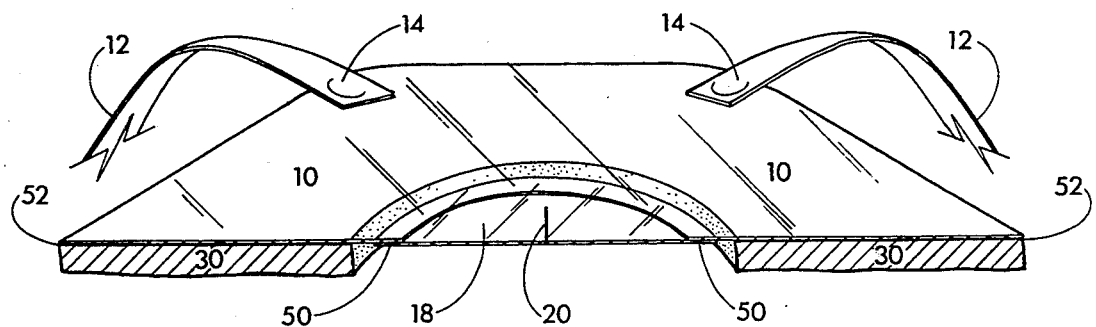
FIG. 5 shows a cross sectional view taken along line A—A of FIG. 1.

FIG. 5 shows a cross sectional view taken along line A—A of FIG. 1. The shield portion 10 is bonded directly, at points 50, to the slotted elastic member. As mentioned earlier, this could all be one piece of elastic material, such as latex, but it is expected that a plastic type material would be used for the shield portion and a rubber section would be used for the slotted elastic member. The fluid absorbent material is shown bonded to the fluid impervious shield at 52. Specific materials and methods of attaching and bonding the individual components can be chosen with regard to compatibility with natural fluids, externally or other applied jellies, creams or other lubricants, Food and Drug Administration guidelines regarding such devices, specific manufacturing procedures or techniques, economics, packaging, and other considerations. Fluid absorbent and impervious materials such as those found in diapers and undergarments would be most useful. The bonds will be adhesives such as glue, thermally or chemically activated, integrally formed pieces, stitching, synthetic rivets, or other suitable sealing and attaching means suitable for sexual and medical devices of a similar nature.

Figure 6:
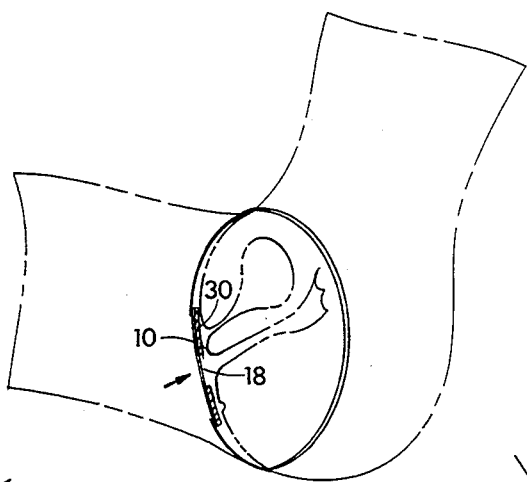
FIG. 6 shows a cross section of an embodiment of the invention as being worn by a female before being penetrated.
Figure 7:
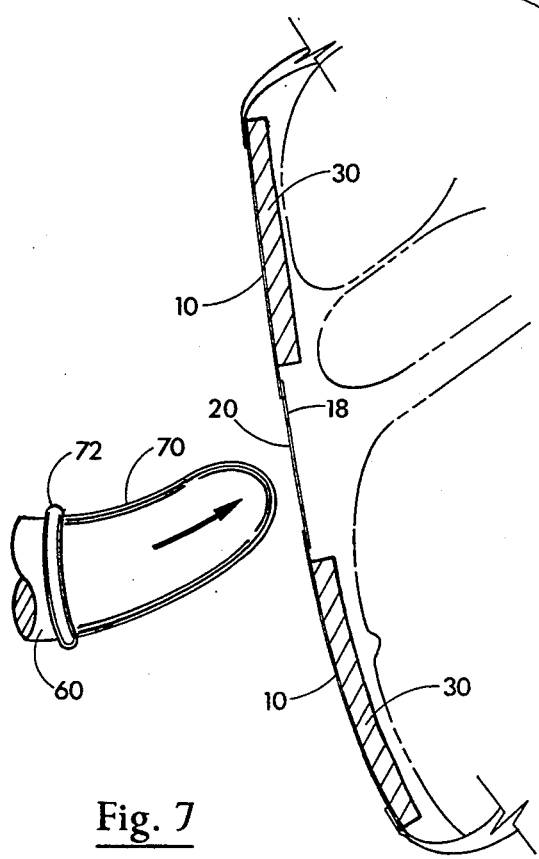
FIG. 7 shows a cross section of an embodiment of the invention in use as it is about to be penetrated by an object wearing a condom or other protective sheath.

FIGS. 6 and 7 show cross sectional views of an embodiment of the invention before being penetrated. As shown, the device would be secured over the orifice to be penetrated with the fluid absorbing element on the inside. The item to be inserted 60 would generally be covered with a condom 70 or some other sheath.

Figure 8:
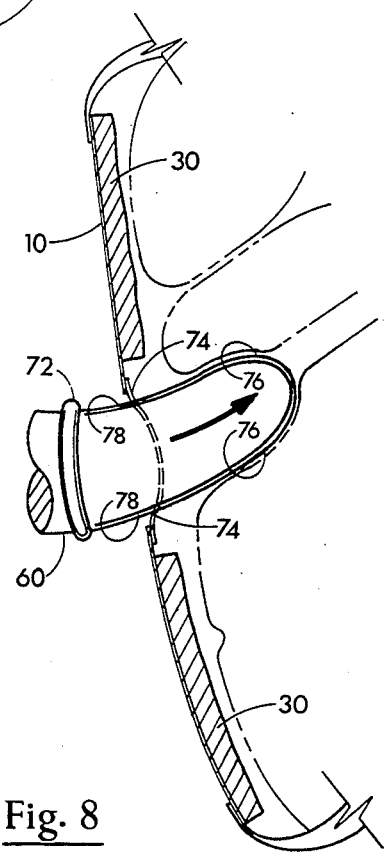
FIG. 8 shows a cross section of an embodiment of the invention in use as it is being penetrated by an object wearing a condom or other protective sheath.

FIG. 8 shows a cross section of an embodiment of the invention in use as it is being penetrated by the probing item, optionally and in the view shown, wearing a condom or other protective sheath. This view shows how the slotted elastic member operates. As penetration occurs, the slot 20 expands only as far as necessary and the material of the elastic slotted member remains in contact with the probing item at 74. Any fluids that would tend to accumulate on the inserted surfaces 76 would be wiped off and would be absorbed by the fluid absorbing material 30. It will be understood that any probing item can be used for penetration and the operation of the device is similar. For example, a male penis covered or not by a condom could be used as well as any portion of a partner's hand, fingers, tongue, prosthetic penis or other sexual device or apparatus, etc. Of course maximum protection from the communication of body fluids would be obtained if the item being inserted is sheathed in rubber, plastic or other covering. The effect of the slotted elastic member is not dissimilar to the operation of a squeegee, and it will produce a squeegee or wiping action on the probing item. Once penetration has occurred, only a minimal amount of body fluids would be withdrawn during the activity. As the inserted item is withdrawn, the slotted elastic member will be squeezed around the item and effectively prevent nearly all of the fluid coating the item used for penetration and withdrawal from being withdrawn as a coating on the probing item. The fluids would thus be retained on the inside of the device and absorbed by the absorbing element. Thus, it is understood that the present invention is not considered to be a contraceptive. It is, however, intended to be used during sexual activity to enhance safety and provide a prophylaxis effect.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A prophylactic device for humans which will allow penetration of body cavities or orifices by a probing item, especially during sexual activity, but will reduce communication of body or other fluids from a user to a partner, said prophylactic device comprising:

a shield member constructed out of a first fluid impervious material and having an upper side and a lower side, said shield member having a predetermined size and shape suitable for covering pubic and other regions surrounding body cavities and orifices;

a fluid absorbing element having an attachment face and a fluid absorbing face, said attachment face attached to said lower side of said shield member by a first attachment means, both said shield member and said fluid absorbing element having a central opening extending therethrough, said central openings having a predetermined size and shape, said central openings having a peripheral region; and a slotted elastic member being constructed of a second fluid impervious material, said second fluid impervious material being somewhat rigid, said slotted elastic member being somewhat larger in size than said central openings, said slotted elastic member being attached to said shield at said peripheral region of said central openings by a second attachment means such that communication of body or other fluids are prevented from passing through said central openings to said upper side of said shield member, said slotted elastic member having a slot with a predetermined length extending therethrough, said slot defining two opposing edges, said slotted elastic member being rigid enough so as to maintain said opposing edges adjacent to and otherwise in contact with each other, whereby when said prophylactic device is placed over said pubic or other regions surrounding cavities or orifices to be penetrated and said penetration accompanying said sexual activity by said probing item occurs, said opposing edges of said slotted elastic member produce a squeegee-like wiping action to remove said body or other fluids from said probing item thereby reducing said communication of said body or other fluids therethrough.

2. The invention of claim 1 wherein said prophylactic device further comprises a retaining means for retaining said prophylactic device in place on said user during use.

3. The invention of claim 2 wherein said retaining means comprises a plurality of extending sections having a predetermined length.

4. The invention of claim 3 wherein said extending sections comprise a flexible elastic material.

5. The invention of claim 3 wherein said predetermined length of said extending sections is adequate to encircle portions of a user's body.

6. The invention of claim 3 wherein said predetermined length of said extending sections is adequate to encircle a user's legs.

7. The invention of claim 2 wherein said retaining means comprises an adhesive.

8. The invention of claim 1 wherein said slot is between approximately ½ and 3 inches in length.

9. The invention of claim 1 wherein said first and second fluid impervious materials are polymeric materials.

10. The invention of claim 1 wherein said first and second fluid impervious materials are rubber materials.

11. The invention of claim 1 wherein said fluid absorbing element comprises an absorbent pad.

12. The invention of claim 1 wherein said fluid absorbing element comprises an absorbent material.

13. The invention of claim 1 wherein said first and second attachment means are adhesives.

14. A prophylactic device for humans which will allow penetration of body cavities or orifices by a probing item, especially during sexual activity, but will reduce communication of body or other fluids from a user to a partner, said prophylactic device comprising:

a shield member constructed out of a fluid impervious material and having an upper side and a lower side, said shield member having a predetermined size and shape suitable for covering pubic and other regions surrounding body cavities and orifices, said shield member having squeegee opening with a predetermined length extending therethrough, said squeegee opening defining two opposing edges, said fluid impervious material being rigid enough so as to maintain said opposing edges adjacent to and otherwise in contact with each other; and a fluid absorbing element having an attachment face and a fluid absorbing face, said attachment face attached to said lower side of said shield member by a first attachment means, whereby when said prophylactic device is placed over said pubic or other regions surrounding cavities or orifices to be penetrated and said penetration accompanying said sexual activity by said probing item occurs, said opposing edges of said squeegee opening in said shield member produce a squeegee-like wiping action to remove said body or other fluids from said probing item thereby reducing said communication of said body or other fluids therethrough.

15. The invention of claim 14 wherein said prophylactic device further comprises a retaining means for retaining said prophylactic device in place on said user.

16. The invention of claim 14 wherein said first attachment means is an adhesive.

* * * * *